(12) United States Patent
Kawai et al.

(10) Patent No.: US 11,812,900 B2
(45) Date of Patent: Nov. 14, 2023

(54) EXCRETION DETECTION SYSTEM AND TOILET SEAT USED IN SAME

(71) Applicant: Panasonic Intellectual Property Management Co., Ltd., Osaka (JP)

(72) Inventors: Masahiro Kawai, Shiga (JP); Wataru Uchiyama, Kyoto (JP)

(73) Assignee: Panasonic Intellectual Property Management Co., Ltd., Osaka (JP)

( * ) Notice: Subject to any disclaimer, the term of this patent is extended or adjusted under 35 U.S.C. 154(b) by 183 days.

(21) Appl. No.: 17/340,143

(22) Filed: Jun. 7, 2021

(65) Prior Publication Data

US 2021/0401244 A1 Dec. 30, 2021

(30) Foreign Application Priority Data

Jun. 25, 2020 (JP) .................. 2020-109219

(51) Int. Cl.
*A47K 13/24* (2006.01)
*A61B 10/00* (2006.01)

(52) U.S. Cl.
CPC .......... *A47K 13/24* (2013.01); *A61B 10/0038* (2013.01)

(58) Field of Classification Search
CPC ............................ A47K 13/24; A61B 10/0038
USPC ........................................................... 4/661
See application file for complete search history.

(56) References Cited

U.S. PATENT DOCUMENTS

| 2018/0271501 A1* | 9/2018 | Wang | G01G 19/00 |
| 2018/0368818 A1* | 12/2018 | Oguri | E03D 11/13 |
| 2021/0134464 A1* | 5/2021 | Kasai | G06F 18/24 |
| 2022/0395149 A1* | 12/2022 | Shimazu | A47K 13/24 |

FOREIGN PATENT DOCUMENTS

| JP | 2017-137707 | | 8/2017 | |
| JP | 2017-137708 A | | 8/2017 | |
| JP | 2021055523 A | * | 4/2021 | ............. A47K 13/24 |
| KR | 10-2019-114132 A | | 10/2019 | |

OTHER PUBLICATIONS

JP-2021055523-A machine English translation printed Feb. 24, 2023 (Year: 2023).*

* cited by examiner

*Primary Examiner* — Christine J Skubinna
(74) *Attorney, Agent, or Firm* — Hamre, Schumann, Mueller & Larson, P.C.

(57) ABSTRACT

Provided is excretion detection system (50) including: toilet seat (10) that is openable; imaging unit (2) with which toilet seat (10) is provided; and information processor (15) that estimates at least one selected from the group consisting of (i) presence or absence of urine or feces, and (ii) a property of the urine or feces, by using imaging data of imaging unit (2), excretion detection system (50) being configured not to capture an image using imaging unit (2) when toilet seat (10) opens.

20 Claims, 11 Drawing Sheets

EXCRETION DETECTION SYSTEM AND TOILET SEAT USED IN SAME

BACKGROUND

1. Technical Field

The present disclosure relates to an excretion detection system that determines presence or absence of excrement in a toilet and properties of the excrement, and a toilet seat used in the excretion detection system.

2. Description of the Related Art

Warm-water washing toilet seats having a function of washing a private part of a human body have been known. FIG. 12 illustrates a warm-water washing toilet seat having a function of washing a private part of a human body. Hereinafter, a configuration of the warm-water washing toilet seat will be described with reference to the drawing.

Warm-water washing toilet seat 500 illustrated in FIG. 12 includes washing toilet seat 110 attached to a toilet bowl, washing nozzle outlet 100, and controller 101. Warm-water washing toilet seat 500 is also provided inside with a washing nozzle and a drive unit. Warm-water washing toilet seat 500 is configured to be able to drive the washing nozzle and adjust washing water jetted from the washing nozzle by using controller 101 depending on a user's preference. This configuration enables warm-water washing toilet seat 500 to arbitrarily wash a private part after excretion.

In recent years, warm-water washing toilet seats have been desired to have various functions added in addition to the above-described washing function. For example, a toilet device of PTL 1 includes a camera facing substantially downward on a toilet seat so that properties of feces are detected from an image of the inside of a toilet bowl acquired by the camera to acquire and present information on a health condition of a user.

Unfortunately, the camera installed substantially downward on the toilet seat faces the front of the toilet bowl when the toilet seat is opened. This causes sensitive information on the user such as the face of the user and the private part of the user urinating to be acquired, so that privacy of the user may be violated. When an acquired image shows information on privacy, the information can be deleted by masking or the like. However, the system acquires the information on privacy once, the user may have remaining anxiety.

CITATION LIST

Patent Literature

PTL 1: Unexamined Japanese Patent Publication No. 2017-137707

SUMMARY

The present disclosure is made to solve a conventional problem as described above, and provides an excretion detection system in which an image is not captured when a toilet seat opens, and a toilet seat used in the excretion detection system. Specifically, the excretion detection system of the present disclosure includes a toilet bowl, a toilet seat that is openable and provided on the toilet bowl, an imaging unit with which the toilet seat is provided, and an information processor that estimates at least one selected from the group consisting of (i) presence or absence of excrement and (ii) a property of the excrement, using imaging data of the imaging unit. The excretion detection system of the present disclosure and the toilet seat used in the excretion detection system are configured such that the imaging unit does not capture an image at least when the toilet seat opens.

The excretion detection system of the present disclosure and the toilet seat used in the excretion detection system enable privacy of a user to be more reliably protected.

DETAILED DESCRIPTION

Hereinafter, exemplary embodiments of the present disclosure will be described with reference to the drawings.

First Exemplary Embodiment

Figure 1:
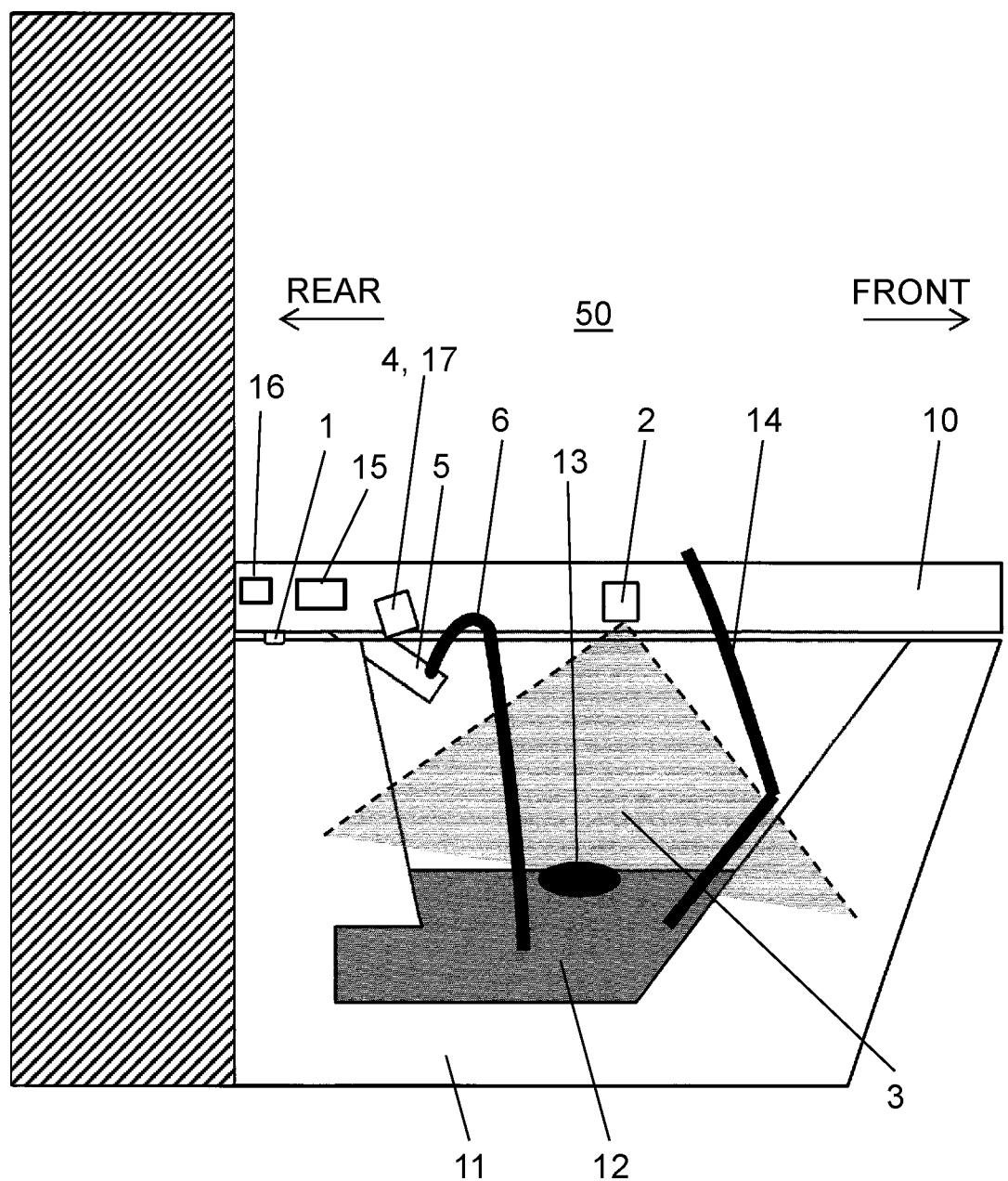
FIG. 1 is a view of an excretion detection system according to a first exemplary embodiment of the present disclosure when a toilet seat is closed as viewed from a lateral side.
Figure 2A:
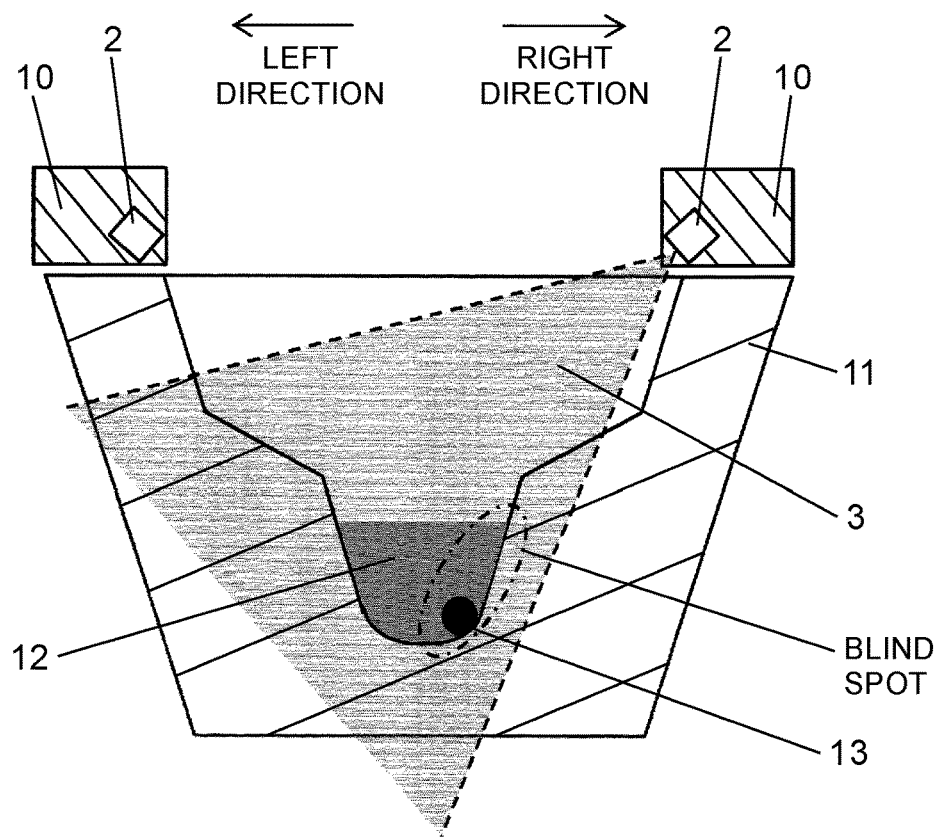
FIG. 2A is a sectional view of the excretion detection system according to the first exemplary embodiment of the present disclosure when the toilet seat is closed, taken along a left-right direction as viewed from a front side.
Figure 2B:
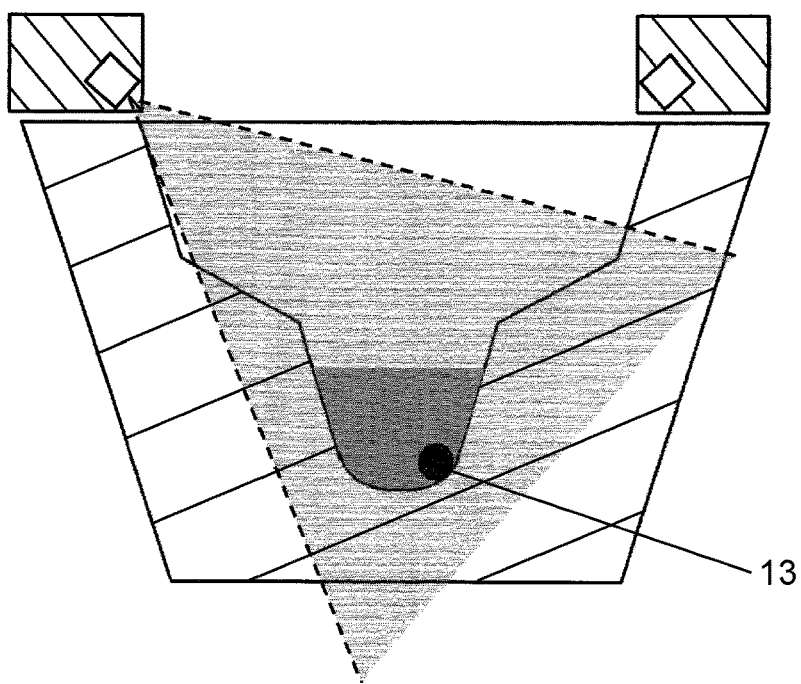
FIG. 2B is a sectional view of the excretion detection system according to the first exemplary embodiment of the present disclosure when the toilet seat is closed, taken along the left-right direction as viewed from the front side.
Figure 3:
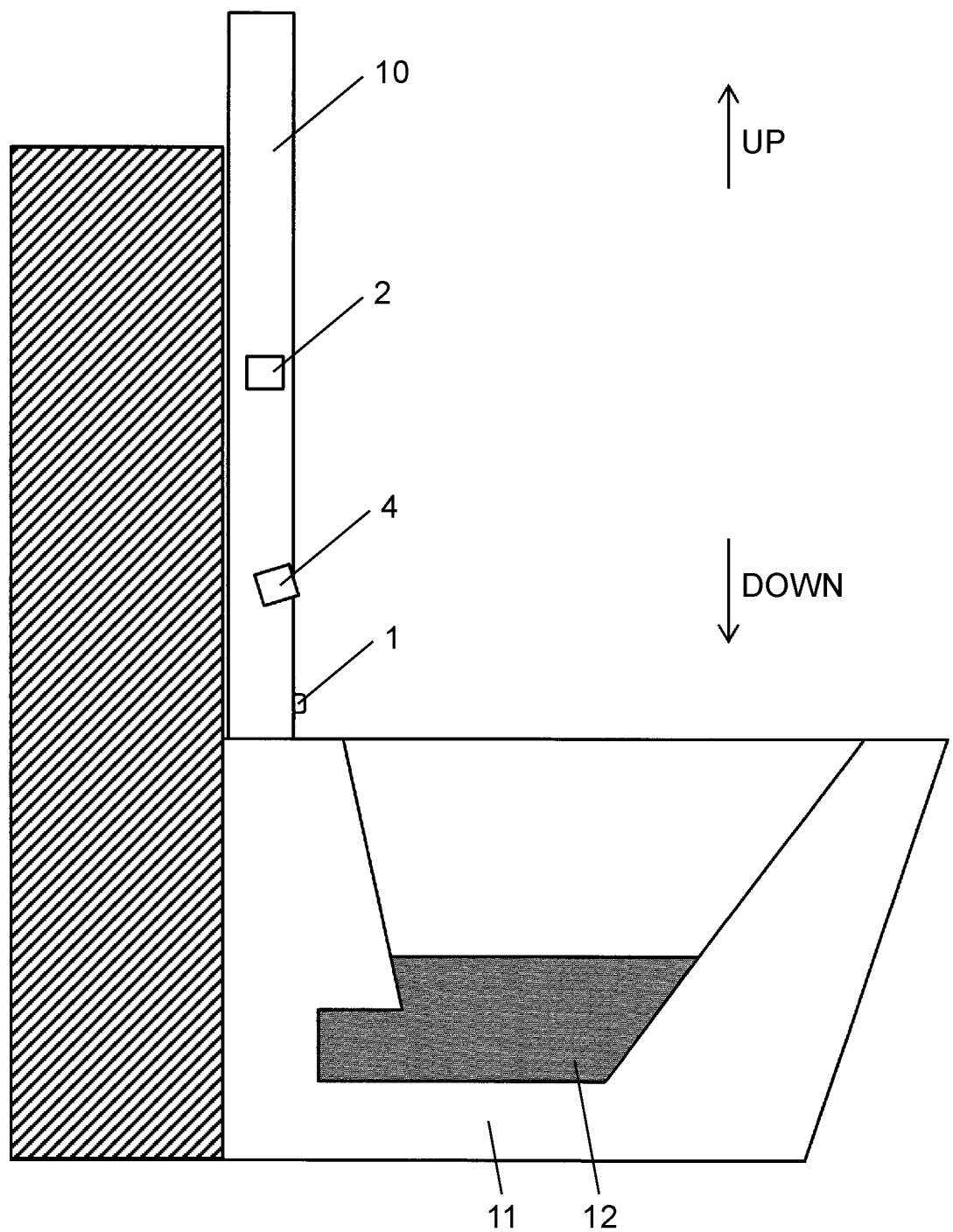
FIG. 3 is a sectional view of the excretion detection system according to the first exemplary embodiment of the present disclosure when the toilet seat opens as viewed from a lateral side.

FIG. 1 is a view of excretion detection system 50 according to a first exemplary embodiment of the present disclosure when a toilet seat closes, as viewed from a lateral side. FIGS. 2A and 2B are each a sectional view of excretion detection system 50 according to the first exemplary embodiment of the present disclosure when the toilet seat closes, taken along a left-right direction as viewed from a front side. FIG. 3 is a sectional view of excretion detection system 50 according to the first exemplary embodiment of the present disclosure when the toilet seat opens, as viewed from the lateral side. Hereinafter, a configuration of excretion detection system 50 according to the present exemplary embodiment will be described.

As illustrated in FIG. 1, excretion detection system 50 includes toilet seat 10 on which a user sits, and toilet bowl 11 that receives excrement. Toilet bowl 11 includes water reservoir 12. FIG. 1 illustrates feces 13 excreted by a user and urine 14 excreted by the user. Excretion detection system 50 also includes information processor 15.

Excretion detection system 50 may include seating detector 1 that detects that a user sits on toilet seat 10. In the present exemplary embodiment, seating detector 1 includes a micro switch configured to be pushed by an upper surface of a peripheral portion of toilet bowl 11 when a user sits on toilet seat 10 and applies its weight thereto. As illustrated in FIG. 3, seating detector 1 protrudes from toilet seat 10 when the user does not sit.

Excretion detection system 50 includes imaging unit 2 such as a camera for detecting at least one of presence or absence of urine or feces, and properties thereof. FIG. 1 illustrates imaging visual field 3 of imaging unit 2, illuminator 4 that illuminates the inside of toilet bowl 11 during capturing an image, and nozzle 5 that discharges private-part washing water 6 for washing a private part of a human body.

In the present exemplary embodiment, one imaging unit 2 is disposed on each of left and right sides in toilet seat 10 as illustrated in FIGS. 2A and 2B. Imaging unit 2 is installed allowing imaging visual field 3 to face an internal space of toilet bowl 11, i.e., to face substantially downward. When imaging visual field 3 is located below an upper surface of toilet bowl 11, imaging visual field 3 may have a center line extending substantially sideways or substantially upward.

Imaging unit 2 is not limited to an RGB image sensor, and another imaging unit, such as a thermal image sensor or a distance image sensor, may be used. Additionally, a zoom mechanism may be added to imaging unit 2. As imaging unit 2, a 4K or 8K high-resolution camera may be used. Such a configuration enables acquiring detailed images such as a surface shape and color of excreted feces. Such a configuration also enables detecting, for example, a minute mass of blood, a mass of fat, and the like that are invisible with naked eyes unless they are brought closer to the naked eyes, and thus enables detailed analysis of feces.

Seating detector 1 may be configured to detect presence or absence of a human body on toilet seat 10 using a sensor such as an illuminance sensor or an ultrasonic sensor. Alternatively, seating detector 1 may use another method such as detecting a urination posture by image processing using a camera.

Operation of excretion detection system 50 configured as described above and toilet seat 10 used therein will be described.

First, when a user approaches the vicinity of excretion detection system 50, a human body detector or the like detects a human body and transmits detected information to information processor 15. When the user sits on toilet seat 10, seating detector 1 detects seating and transmits seating detection information to information processor 15.

Information processor 15 turns on illuminator 4 and starts processing of acquiring an image using imaging unit 2. Examples of the image include a still image and a moving image captured at regular intervals or under predetermined conditions. Although examples of the predetermined conditions include when a temperature change inside toilet bowl 11 is detected by an infrared sensor provided in toilet seat 10, the predetermined conditions are not limited to this. When a private part is washed using nozzle 5 during use of a toilet in which excretion detection system 50 is installed, information on the washing may be transmitted to information processor 15.

Information processor 15 analyzes a captured image, and estimates presence or absence of urine and feces, and properties related to excrement, such as a shape and color of the excrement.

Examples of a method for analyzing an image include predetermined threshold processing based on image information. The examples include analysis methods such as detecting presence or absence of feces, or the amount of feces from presence or absence of a brown region, or an area of the brown region, in an image, and determining whether there are bloody feces from presence or absence of a red region in an image. The image may be analyzed by other methods such as machine learning and deep learning.

The estimated result of the properties related to the excrement is transmitted to a personal computer, a smartphone, an information presentation unit provided in the toilet in which excretion detection system 50 is installed, and the like by communication, and is presented to the user. At that time, health conditions or the like of the user estimated based on the properties of the excrement may be presented.

As illustrated in FIGS. 2A and 2B, toilet bowl 11 generally has a valley shape. Toilet bowl 11 may have a portion with a large gradient near water reservoir 12. Toilet bowl 11 having such a structure forms a blind spot as indicated by a one-dot chain line in FIG. 2A when viewed from a certain imaging unit 2. Thus, when feces 13 fall in the blind spot, the feces may not be detected. In particular, a product form having toilet seat 10 configured separately from toilet bowl 11 is required to cope with toilet bowls 11 having various shapes, so that this problem is likely to occur.

Then, in the present exemplary embodiment, one imaging unit 2 is disposed on each of the left and right sides of toilet seat 10 as illustrated in FIGS. 2A and 2B. As illustrated in FIG. 2B, such a configuration enables imaging unit 2 on the left side as viewed from the front of toilet seat 10 to capture an image of a blind spot of imaging unit 2 on the right side as viewed from the front of toilet seat 10 as illustrated in FIG. 2A. Such a configuration enables capturing characteristics of local urine and feces, such as adhesion of small feces or blood hidden in the blind spot of imaging unit 2 on the right side. This enables improving determination accuracy of presence or absence of excrement and properties thereof. When imaging units 2 are each disposed at a substantially symmetrical position with respect to water reservoir 12, a blind spot area can be more effectively reduced.

When information processor 15 estimates presence or absence of excrement and properties thereof, it is preferable to use not only captured image data but also state detection information on a toilet in which excretion detection system 50 is installed, such as information on seating and information on use of a private-part washing function. This enables providing excretion detection system 50 in which erroneous detection of excrement is reduced and determination accuracy of urine and feces is improved.

For example, private-part washing water 6 discharged from nozzle 5 is likely to be erroneously detected due to its appearance similar to that of urine. Thus, erroneous detection can be prevented by not determining presence or absence of urine while the private-part washing function is used. Some of washing tools, such as a scrubbing brush used for washing toilet bowl 11, are likely to be erroneously detected due to its color and the like similar to those of feces. However, using the information on seating enables determining that an image captured in a non-seated state does not show feces, so that erroneous detection can be prevented.

Additionally, watery diarrhea belonging to feces is similar to urine in dark color, and thus discrimination between urine and feces is likely to be mistaken. When containing solid matter or floating matter, diarrhea feces can be determined as feces from their image. However, there is a rare case where no solid material is contained. Thus, when diarrhea feces having no solid material can be determined as feces, urine is also likely to be determined as feces. Thus, watery matter in a non-seated state is determined as urine using the information on seating to prevent erroneous detection of urine as feces, so that determination accuracy can be improved.

Examples of available information on usage status of a toilet in which excretion detection system 50 is installed include open and close status of a lid of a toilet seat, open and close status of the toilet seat, usage status of a toilet-bowl washing function, use of toilet paper, a seating posture of a user, and sex and age of the user.

When the user stands up from toilet seat 10 after excretion, seating detector 1 detects a non-seated state. Based on such detection, information processor 15 turns off illuminator 4, and ends image acquisition processing using imaging unit 2.

As described above, excretion detection system 50 of the present exemplary embodiment and toilet seat 10 used therein are configured such that imaging unit 2 does not capture an image at least when toilet seat 10 opens. Excretion detection system 50 of the present exemplary embodiment and toilet seat 10 used therein may be configured such that an image is captured only while seating detector 1 determines that a user sits. Such a configuration prevents an image of a face, a private part, or the like of a user from being captured in a state where toilet seat 10 is opened and imaging unit 2 faces forward, so that privacy can be protected. As illustrated in FIG. 1, excretion detection system 50 may be configured not to capture an image in a state where a user does not sit even when toilet seat 10 closes. Such a configuration prevents an image from being captured even when a user puts a part of a body such as a hand or a face into toilet bowl 11. This also enables preventing an image of a human body from being captured when the human body is reflected by a water surface in toilet bowl 11. Thus, such a configuration enables privacy to be more reliably protected.

Instead of capturing an image while seating detector 1 determines that a user sits, the capturing an image may be controlled such that the image is not captured while toilet seat 10 opens on the basis of detection using toilet seat open-close detector 16 that is provided in excretion detection system 50 and toilet seat 10 used therein, and that detects whether toilet seat 10 opens or closes. In this case, information processor 15 may instruct a start of capturing an image, for example, when an occupancy detector that detects entry of a person into a toilet provided with excretion detection system 50 detects entry of a person. Alternatively, a start of capturing an image may be instructed when a temperature change is detected by a sensor for detecting a temperature change in toilet bowl 11, such as an infrared sensor provided in excretion detection system 50 and toilet seat 10 used therein. Information processor 15 can instruct a start of capturing an image at an appropriate timing while toilet seat 10 is closed. Even a control method as described above prevents an image from being captured in a state where toilet seat 10 is opened and imaging unit 2 faces forward in excretion detection system 50 and toilet seat 10 used therein, so that privacy can be protected.

When illuminator 4 is configured to be turned on only during processing of capturing an image as in the present exemplary embodiment, illuminator 4 also serves as imaging notification unit 17 that notifies a user that an image is being captured. Illuminator 4 of the present exemplary embodiment is turned off except during capturing an image, so that the user can be more explicitly notified of a state of capturing an image, and thus a sense of security can be enhanced. Imaging notification unit 17 may be configured to notify a user by means such as a red-light emitting diode (LED) of a camera body used as imaging unit 2, a display of an imaging status on a toilet seat remote controller or the like, or a sound.

Figure 4:
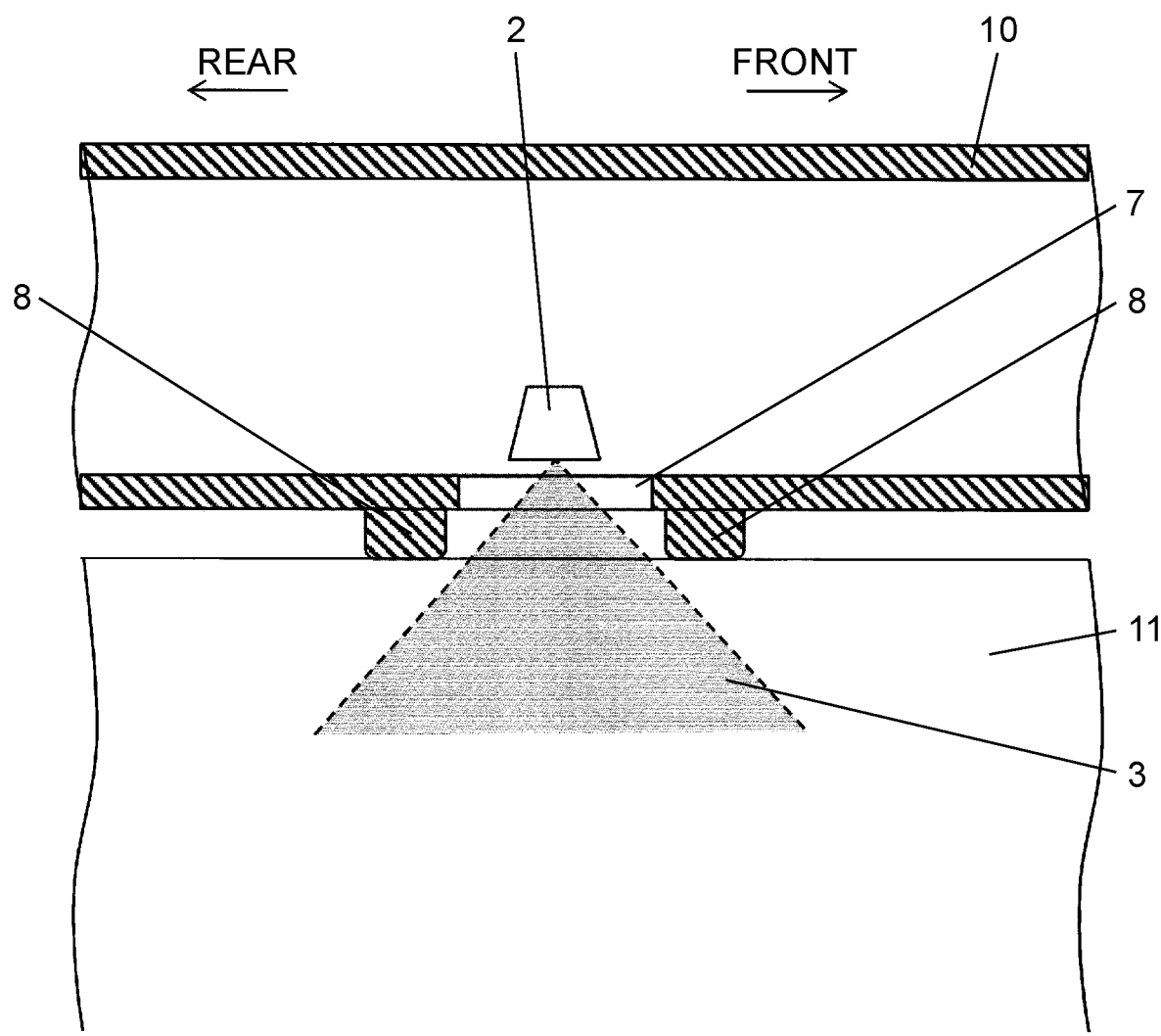
FIG. 4 is a partial sectional view of a periphery of an imaging unit of the excretion detection system according to the first exemplary embodiment of the present disclosure when the toilet seat is closed.

FIG. 4 is a partial sectional view of a periphery of imaging unit 2 of excretion detection system 50 according to the first exemplary embodiment of the present disclosure. As illustrated in FIG. 4, excretion detection system 50 and toilet seat 10 used therein may include lens cover 7 disposed in an imaging direction of imaging notification. Lens cover 7 may be formed integrally with imaging unit 2. When imaging unit 2 is disposed in toilet seat 10, toilet seat 10 is required to have an opening to secure a visual field of imaging unit 2. Then, even when the opening is closed by lens cover 7, toilet seat 10 decreases in strength.

When a heavy person sits on toilet seat 10, or when a load is locally applied to toilet seat 10 by a hand of a user when the user falls, toilet seat 10 may be deformed to cause lens cover 7 to be cracked, and thus the inside of toilet bowl 11 cannot be visually recognized. When the load is large, imaging unit 2 may be broken.

Thus, in the present exemplary embodiment, toilet seat deformation preventing structure 8 for preventing deformation of toilet seat 10 may be provided as illustrated in FIG. 4. Specifically, in the present exemplary embodiment, at least one support leg protruding substantially downward from toilet seat 10 is provided around lens cover 7, as toilet seat deformation preventing structure 8. When a load is applied to toilet seat 10 from above while toilet seat 10 is closed, toilet seat deformation preventing structure 8 comes into contact with toilet bowl 11 and prevents toilet seat 10 from being further deformed. This enables preventing lens cover 7 from being cracked, the inside of toilet bowl 11 from being unable to be visually recognized, and imaging unit 2 from being broken. Toilet seat 10 may be increased in strength by another method such as attaching a member having high strength, such as a metal plate, to the inside of toilet seat 10, or increasing thickness of toilet seat 10.

When a toilet in which excretion detection system 50 is installed is used and feces 13, urine 14, or private-part washing water 6 falls into toilet bowl 11, water in water reservoir 12 may be repelled and adhere to lens cover 7 of imaging unit 2. Thus, excretion detection system 50 and toilet seat 10 used therein may be configured to notify a user through a personal computer, a smartphone, or the like when information processor 15 detects that imaging visual field 3 of imaging unit 2 is blocked by a predetermined area or more.

Such a configuration causes adhesion of urine, feces, or water droplets to lens cover 7 to be notified at an early stage to promote washing of a lens by a user, so that excretion can be prevented from being unable to be detected. Alternatively, such a configuration enables preventing a state in which excretion cannot be detected from continuing for a long period of time. For example, a method for detecting that imaging visual field 3 of imaging unit 2 is blocked by a predetermined area or more may be configured to integrate luminance of the entire captured image at timing when use of a toilet in which excretion detection system 50 is installed is finished, and determine that a contamination is attached when the luminance is darker than a predetermined value. Alternatively, the determination may be made by another method, such as other image processing, machine learning, or deep learning.

Excretion detection system 50 of the present disclosure and toilet seat 10 used therein do not capture an image when toilet seat 10 is opened, so that estimation of properties of urine discharged in a standing posture is difficult. However, many users, such as a woman, an elderly person, a person requiring care, and a man who does not urinate in a standing posture, can enjoy usefulness of excretion detection system 50 without any trouble. When estimation of properties of urine discharged in a standing posture is required, excretion detection system 50 and toilet seat 10 used therein may be configured to restrict an orientation of imaging unit 2 by changing the orientation of imaging unit 2 to a substantially downward direction with an actuator or the like, or changing an imaging range of imaging unit 2 to a downward range by software processing, when toilet seat 10 is opened. Alternatively, imaging unit 2 may be installed in a body part other than an opening-closing part of toilet seat 10, or toilet bowl 11.

Excretion detection system 50 of the present exemplary embodiment and toilet seat 10 used therein may be configured to create three-dimensional shape data on feces from images captured by left and right imaging units 2. Such a configuration enables analyzing a shape of feces in more detail, and estimating the amount of feces more accurately.

In the present exemplary embodiment, excretion detection system 50 includes toilet bowl 11, toilet seat 10 that is openable and provided on toilet bowl 11, imaging unit 2 installed in toilet seat 10, and information processor 15 that estimates at least one of presence or absence of excrement, and properties of the excrement, using imaging data of imaging unit 2, and imaging unit 2 is configured not to capture an image at least when toilet seat 10 opens.

Such a configuration prevents an image of a face or a private part of a user from being captured when toilet seat 10 is opened, so that privacy of the user can be protected.

Excretion detection system 50 of the present exemplary embodiment and toilet seat 10 used therein may include toilet seat open-close detector 16 that detects whether toilet seat 10 opens or closes. Excretion detection system 50 and toilet seat 10 used therein may be configured such that, when toilet seat open-close detector 16 detects that toilet seat 10 opens or closes, imaging unit 2 does not capture an image while toilet seat 10 opens. As toilet seat open-close detector 16, a toilet seat open-close detection function generally mounted on a toilet seat may be used. In this case, excretion detection system 50 of the present disclosure and toilet seat 10 used therein can be implemented without adding an additional component.

Such a configuration enables reducing a number of components, cost, and component space.

Excretion detection system 50 of the present exemplary embodiment and toilet seat 10 used therein may include seating detector 1 that detects whether a user sits. Excretion detection system 50 of the present exemplary embodiment and toilet seat 10 used therein may be configured such that imaging unit 2 does not capture an image in a non-seated state.

As seating detector 1, a seating detection function widely mounted on a conventional toilet seat may be used. In this case, excretion detection system 50 of the present disclosure and toilet seat 10 used therein can be implemented without adding an additional component, and the number of components, cost, and component space can be reduced. Such a configuration does not allow capturing an image even when toilet seat 10 is closed and a user does not sit, so that an image is not captured even when the user puts a part of its body such as a hand or a face into toilet bowl 11. This configuration also enables preventing capturing an image of a human body when it is reflected by a water surface in toilet bowl 11, so that privacy can be protected more reliably.

Excretion detection system 50 of the present exemplary embodiment and toilet seat 10 used therein may include blocking part 21 (described later) that blocks imaging visual field 3 of imaging unit 2 when toilet seat 10 opens (see FIG. 5).

Such a configuration causes imaging visual field 3 of imaging unit 2 to blocked when toilet seat 10 opens, so that imaging unit 2 becomes invisible to a user. Thus, the user can use the toilet seat without feeling uneasy about whether an image is being captured, so that the sense of security can be further enhanced.

Excretion detection system 50 of the present exemplary embodiment and toilet seat 10 used therein include blocking part 21 that may be located at a position to block imaging visual field 3 of imaging unit 2 when toilet seat 10 opens.

Such a configuration causes imaging unit 2 to be blocked and become invisible even when toilet seat 10 is opened in a non-energized state, so that the sense of security can be further enhanced.

Excretion detection system 50 of the present exemplary embodiment and toilet seat 10 used therein may also include imaging notification unit 17 that notifies imaging using imaging unit 2. Such a configuration enables a user to be more explicitly notified of a state of capturing an image, so that the sense of security can be further enhanced.

Excretion detection system 50 of the present exemplary embodiment includes toilet bowl 11, toilet seat 10 that is openable and provided on toilet bowl 11, imaging unit 2 installed in toilet seat 10, and information processor 15 that estimates at least one of presence or absence of excrement, and properties of the excrement, using imaging data of imaging unit 2. Excretion detection system 50 of the present exemplary embodiment may include a plurality of imaging units 2. Excretion detection system 50 of the present exemplary embodiment may be configured to capture an image of the inside of toilet bowl 11 from a plurality of angles using the plurality of imaging units 2.

Such a configuration enables reducing an area of a blind spot in the visual field of imaging unit 2, so that characteristics of small feces, or a part of urine or feces, can be captured. Thus, determination accuracy of presence or absence of excrement and properties thereof can be improved.

Excretion detection system 50 of the present exemplary embodiment and toilet seat 10 used therein may be configured such that at least one imaging unit 2 may be arranged on each of left and right sides with respect to a center line in the left-right direction when viewed from a front side of toilet seat 10.

Such a configuration facilitates capturing an image of portions near inner surfaces of toilet bowl 11 on the left and right sides in water reservoir 12 in toilet bowl 11, the portions being likely to be a blind spot, so that an area of the blind spot of the visual field of imaging unit 2 can be effectively reduced.

Excretion detection system 50 of the present exemplary embodiment includes toilet bowl 11, toilet seat 10 that is openable and provided on toilet bowl 11, imaging unit 2 installed in toilet seat 10, and information processor 15 that estimates at least one of presence or absence of excrement, and properties of the excrement, using imaging data of imaging unit 2. Excretion detection system 50 of the present exemplary embodiment and toilet seat 10 used therein may include toilet seat deformation preventing structure 8 for preventing deformation of toilet seat 10, being disposed around imaging unit 2.

Such a configuration enables preventing deformation of toilet seat 10 when a load is applied to the vicinity of imaging unit 2, and preventing a lens of imaging unit 2 from being cracked, the inside of toilet bowl 11 from being unable to be visually recognized, and imaging unit 2 from being broken.

Excretion detection system 50 of the present exemplary embodiment includes toilet bowl 11, toilet seat 10 that is openable and provided on toilet bowl 11, imaging unit 2 installed in toilet seat 10, lens cover 7 that protects the lens of imaging unit 2, and information processor 15 that estimates at least one of presence or absence of excrement, and properties of the excrement, using imaging data of imaging unit 2. Excretion detection system 50 of the present exemplary embodiment and toilet seat 10 used therein may be configured to detect that the visual field of imaging unit 2 is blocked by a predetermined area or more by blocking part 21 or lens cover 7 to which a contamination adheres, or the like, and notify a user of the fact. Such detection is performed by information processor 15 based on an image captured by imaging unit 2, for example. Such notification is performed, for example, on a user interface such as a user's information terminal, an operation unit of toilet seat 10, a remote controller, or the like.

Such a configuration causes adhesion of urine, feces, or water droplets to the lens of imaging unit 2 to be notified at an early stage to promote washing of a lens by a user, so that excretion can be prevented from being unable to be detected. Alternatively, such a configuration enables preventing a state in which excretion cannot be detected from continuing for a long period of time.

Second Exemplary Embodiment

Figure 5:
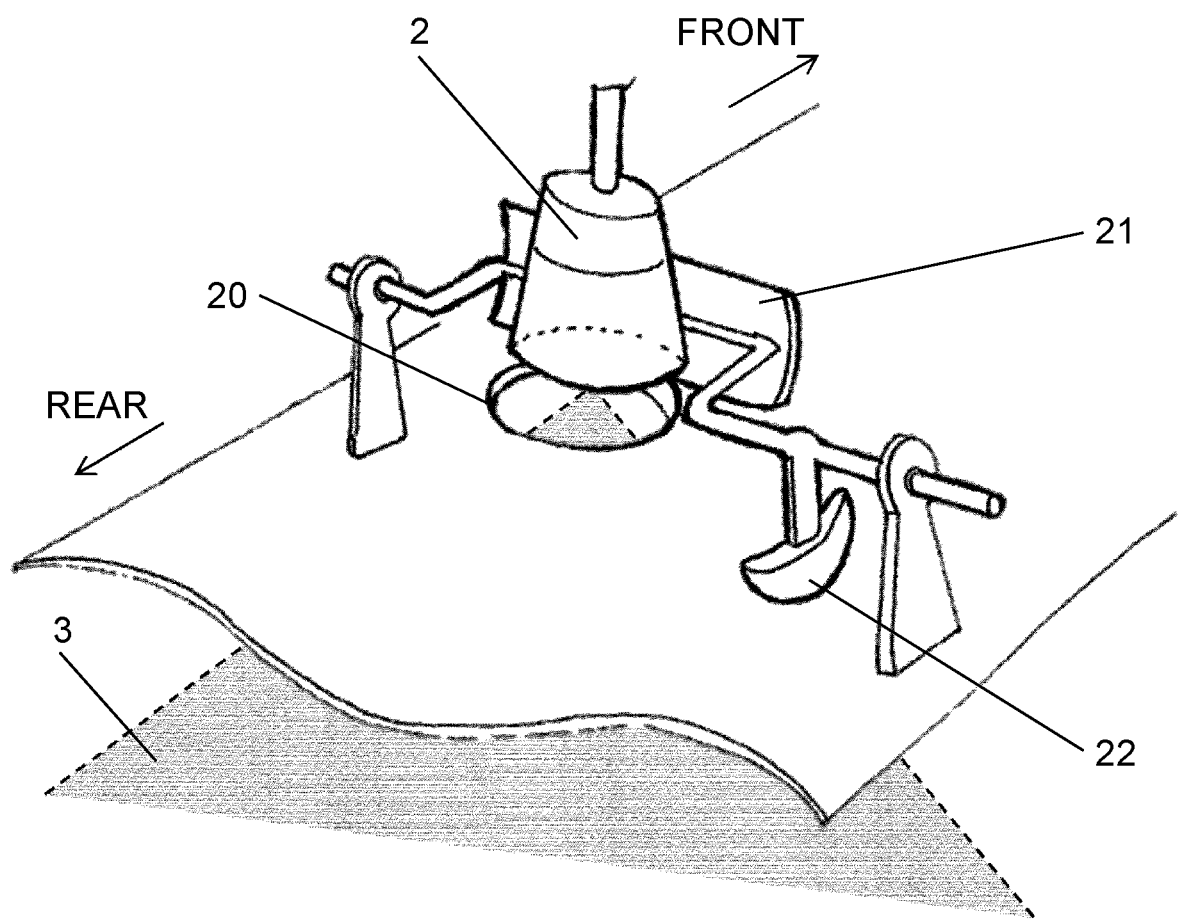
FIG. 5 is a schematic view for illustrating a structure around an imaging unit of an excretion detection system according to a second exemplary embodiment of the present disclosure when a toilet seat is closed.
Figure 6:
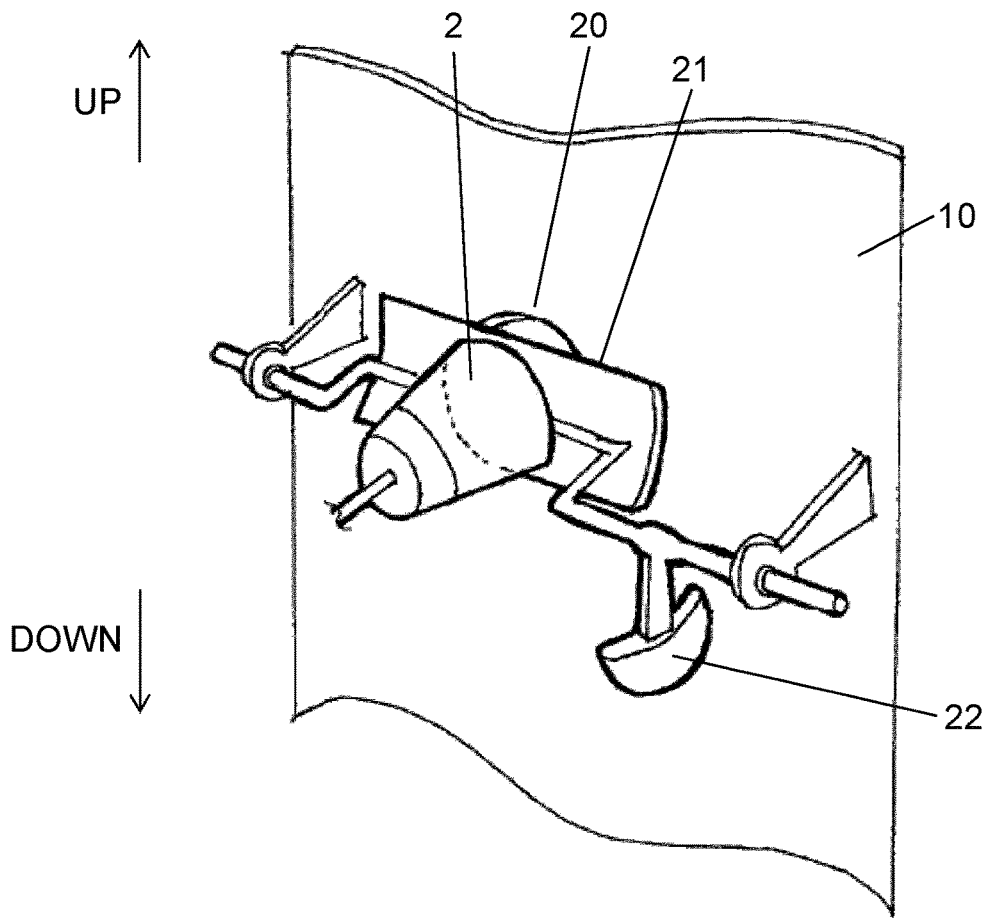
FIG. 6 is a schematic view for illustrating a structure around the imaging unit of the excretion detection system according to the second exemplary embodiment of the present disclosure when the toilet seat opens.

FIG. 5 is a schematic view illustrating a structure around imaging unit 2 inside a toilet seat when the toilet seat closes, the toilet seat being used in excretion detection system 50 according to a second exemplary embodiment of the present disclosure. FIG. 6 is a schematic view for illustrating a structure around imaging unit 2 inside the toilet seat when the toilet seat opens, the toilet seat being used in excretion detection system 50 according to the second exemplary embodiment of the present disclosure.

Hereinafter, a configuration of excretion detection system 50 according to the present exemplary embodiment and toilet seat 10 used therein will be described. Description of a configuration and operation similar to those of the first exemplary embodiment will be eliminated.

FIG. 5 illustrates toilet seat 10 having a lower surface provided with opening 20 at a portion intersecting imaging visual field 3 of imaging unit 2. Excretion detection system 50 according to the present exemplary embodiment and toilet seat 10 used therein are configured such that imaging unit 2 can capture an image of the inside of toilet bowl 11 through opening 20. Excretion detection system 50 according to the present exemplary embodiment and toilet seat 10 used therein further include blocking part 21 configured to be able to block imaging visual field 3 of imaging unit 2. As illustrated in FIG. 5, excretion detection system 50 according to the present exemplary embodiment and toilet seat 10 used therein may be configured such that blocking part 21 does not block imaging visual field 3 due to weight of weight 22.

Operation of excretion detection system 50 configured as described above and toilet seat 10 used therein will be described.

When a user sits on toilet seat 10, seating detector 1 detects seating, and then information processor 15 causes imaging unit 2 to start the image acquisition processing based on the detection of the seating. At this time, as illustrated in FIG. 5, when blocking part 21 is in a state where imaging visual field 3 is not blocked due to the weight of weight 22, an image of the inside of toilet bowl 11 can be captured by imaging unit 2. Excretion detection system 50 may be configured to start capturing an image using imaging unit 2 at another timing, such as when an occupancy detector that detects entry of a person into a toilet in which excretion detection system 50 is installed detects entry of a person.

When a user stands up from toilet seat 10 after defecation, seating detector 1 detects a non-seated state, and then information processor 15 ends the image acquisition processing using imaging unit 2 based on the detection of the non-seated state.

When a user opens toilet seat 10 in another use scene of excretion detection system 50, as illustrated in FIG. 6, weight 22 turns downward by its own weight, and then blocking part 21 blocks opening 20 to block imaging visual field 3 of imaging unit 2. This causes imaging unit 2 to be invisible from the user when toilet seat 10 is opened, so that the user can use the toilet without insecure feeling that an image may be captured, and thus the sense of security can be further enhanced. Blocking part 21 includes a physical structure, so that imaging unit 2 is blocked by blocking part 21 to be invisible even when toilet seat 10 is opened in a non-energized state. As described above, excretion detection system 50 of the present exemplary embodiment and toilet seat 10 used therein are configured such that imaging unit 2 is invisible from the user even in the non-energized state, so that the sense of security can be further enhanced. Excretion detection system 50 of the present exemplary embodiment and toilet seat 10 used therein are configured such that blocking part 21 blocks opening 20 to block imaging visual field 3 of imaging unit 2. Such a configuration enables reducing a contamination or the like on the lens of imaging unit 2.

Figure 7:
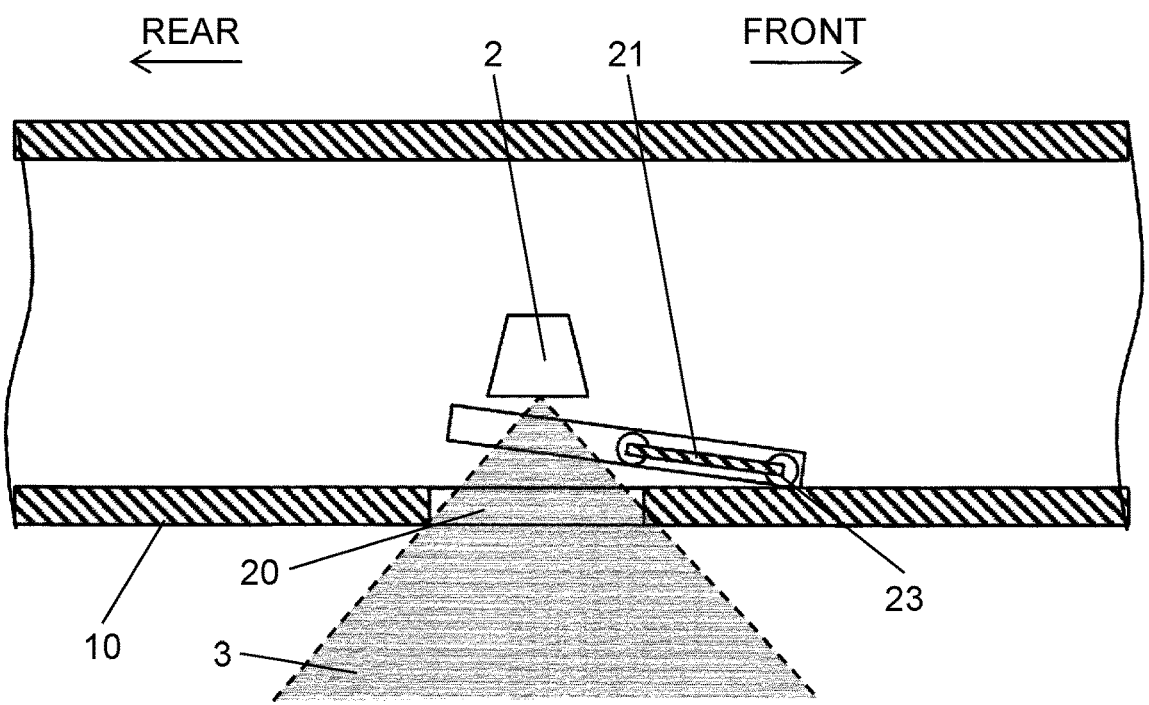
FIG. 7 is a sectional view for illustrating a structure around the imaging unit of the excretion detection system according to the second exemplary embodiment of the present disclosure when the toilet seat is closed.
Figure 8:
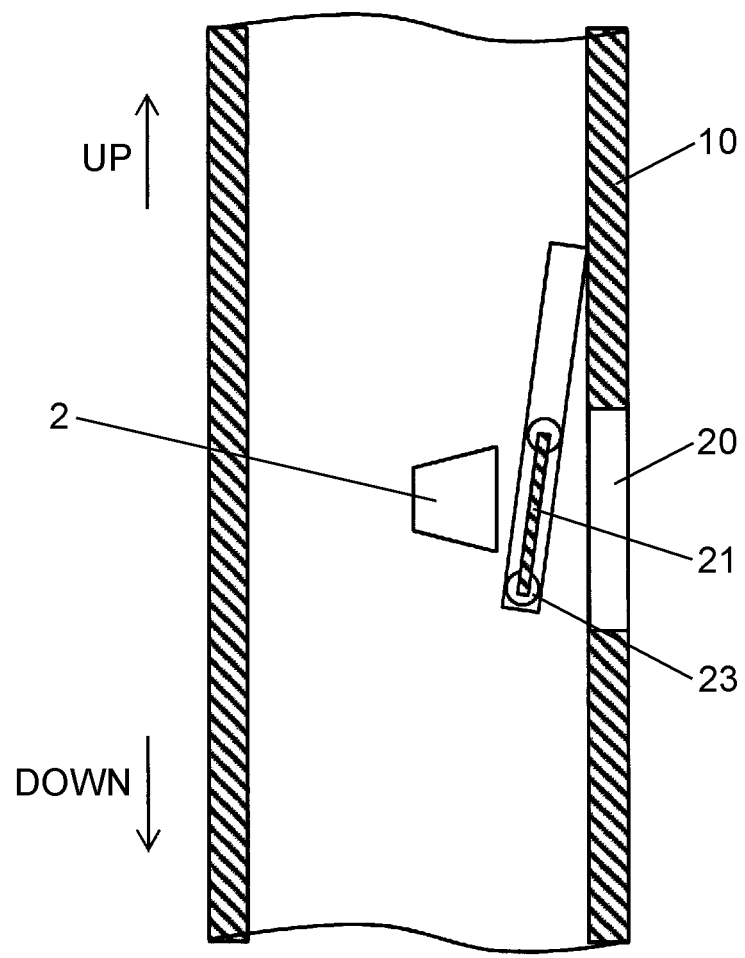
FIG. 8 is another sectional view for illustrating a structure around the imaging unit of the excretion detection system according to the second exemplary embodiment of the present disclosure when the toilet seat opens.
Figure 9:
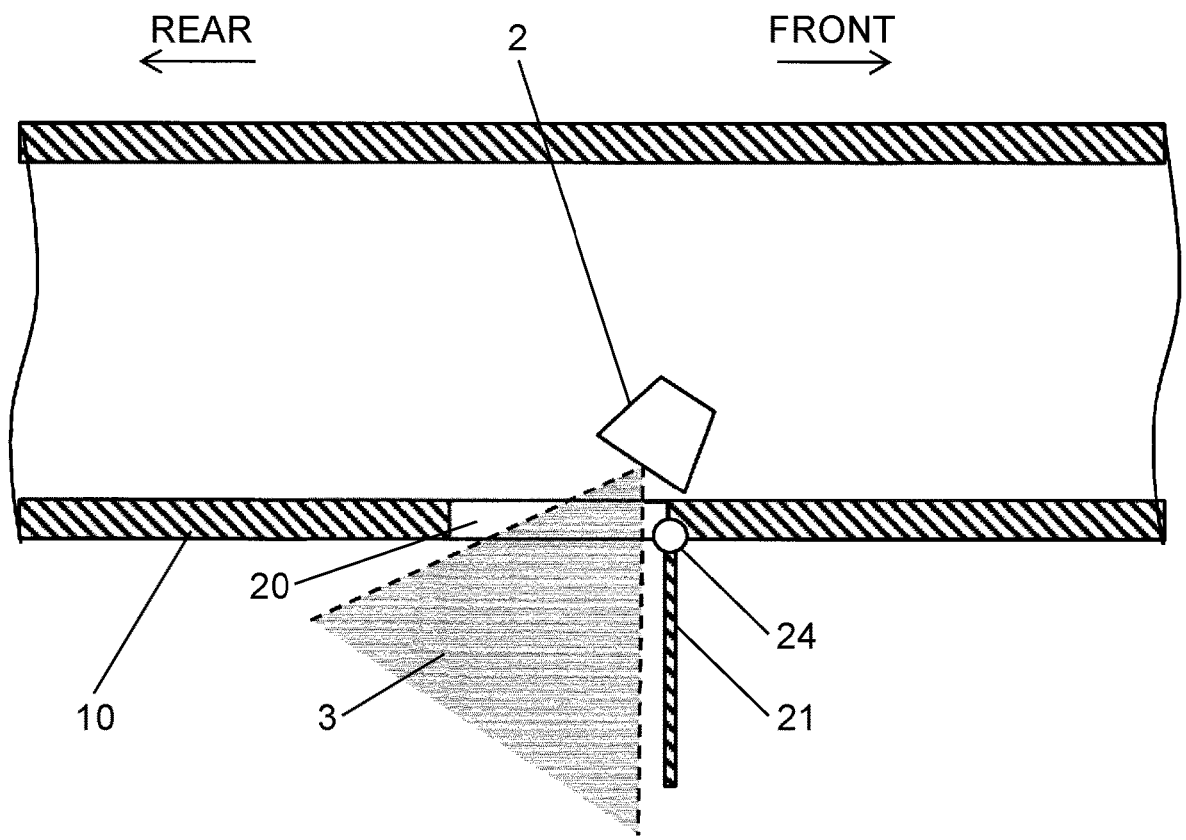
FIG. 9 is yet another sectional view for illustrating a structure around the imaging unit of the excretion detection system according to the second exemplary embodiment of the present disclosure when the toilet seat is closed.
Figure 10:
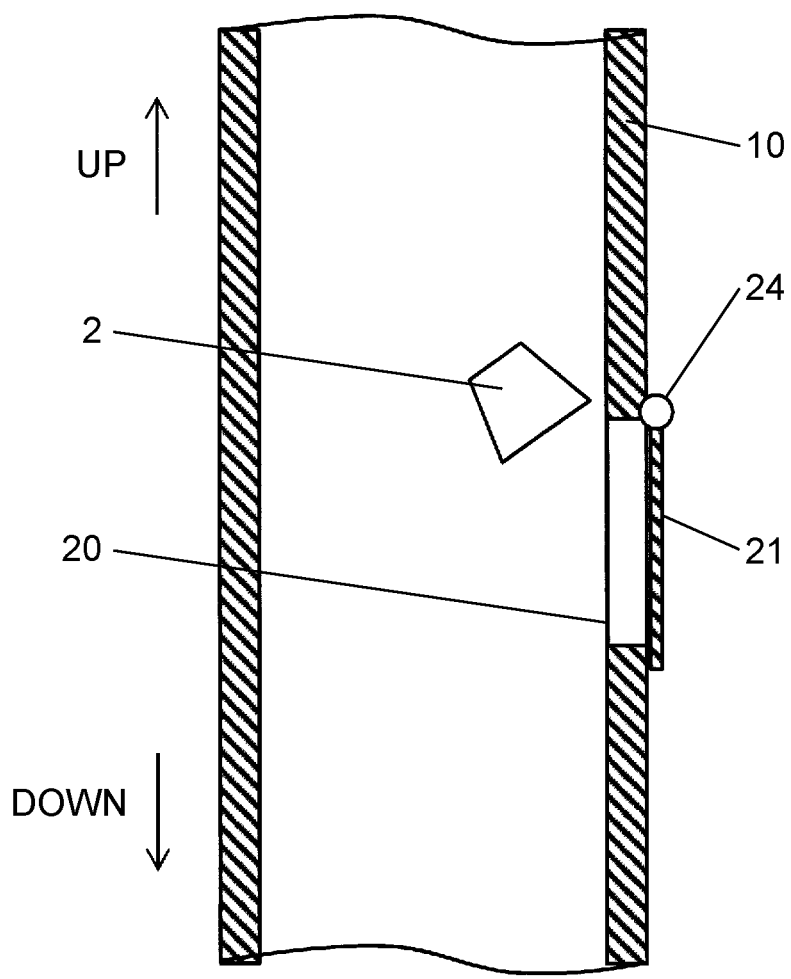
FIG. 10 is yet another sectional view for illustrating a structure around the imaging unit of the excretion detection system according to the second exemplary embodiment of the present disclosure when the toilet seat opens.

As illustrated in FIGS. 7 and 8, blocking part 21 may include wheel 23 that turns by its own weight about a central portion of blocking part 21. As illustrated in FIGS. 9 and 10, blocking part 21 may include hinge 24 on the front side of toilet seat 10 to turn by its own weight about hinge 24. Although blocking part 21 configured to turn by its own weight is exemplified in the present exemplary embodiment, excretion detection system 50 and toilet seat 10 used therein may be configured to open and close blocking part 21 by another mechanism such as a spring or a link mechanism. Excretion detection system 50 and toilet seat 10 used therein may be configured such that opening and closing of blocking part 21 is controlled by a drive unit such as a motor, or blocking part 21 may be made of a material that can be changed in transparency by energization as in a liquid crystal shutter.

Excretion detection system 50 of the present exemplary embodiment and toilet seat 10 used therein are configured such that blocking part 21 prevents an image of a face, a private part, or the like of a user from being captured by physical means or a mechanism when toilet seat 10 is opened. Such a configuration prevents an image of a face, a private part, or the like of a user from being captured when toilet seat 10 opens, which is one of predetermined conditions, regardless of imaging control of imaging unit 2, even when imaging unit 2 is controlled to always capture an image during energization, and thus privacy can be protected.

In the present exemplary embodiment, excretion detection system 50 and toilet seat 10 used therein include blocking part 21. Blocking part 21 may be configured to block imaging visual field 3 of imaging unit 2 when toilet seat 10 opens.

Such a configuration causes imaging unit 2 to be blocked to be invisible from a user when toilet seat 10 is opened, so that the user does not have insecure feeling that an image may be captured, and thus the sense of security can be further enhanced.

Blocking part 21 may be provided at a position where imaging visual field 3 of imaging unit 2 is blocked when toilet seat 10 opens.

Such a configuration causes imaging unit 2 to be blocked and become invisible even when toilet seat 10 is opened in a non-energized state, so that the sense of security can be further enhanced.

Third Exemplary Embodiment

Figure 11:
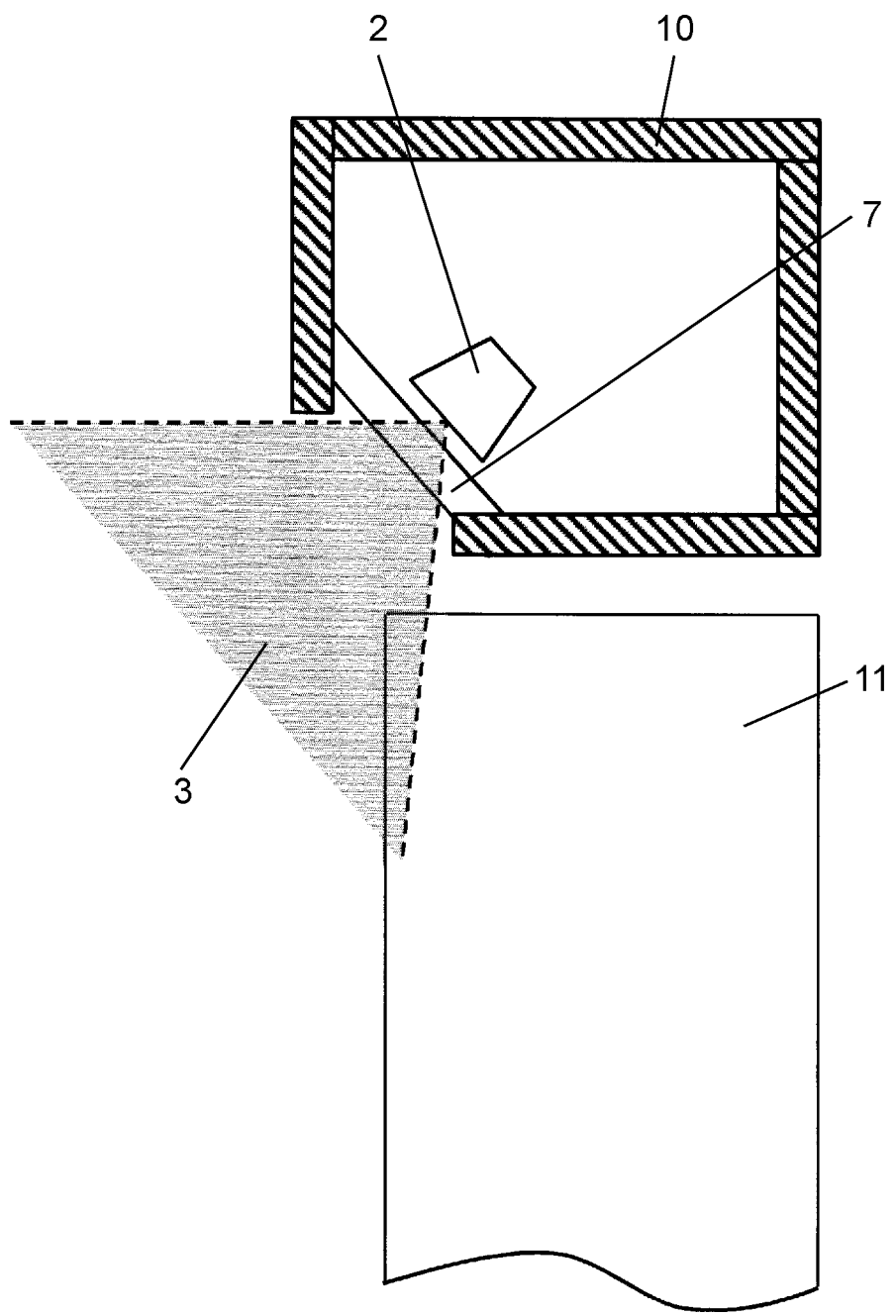
FIG. 11 is a sectional view for illustrating a structure around an imaging unit of an excretion detection system according to a third exemplary embodiment of the present disclosure when a toilet seat is closed.
Figure 12:
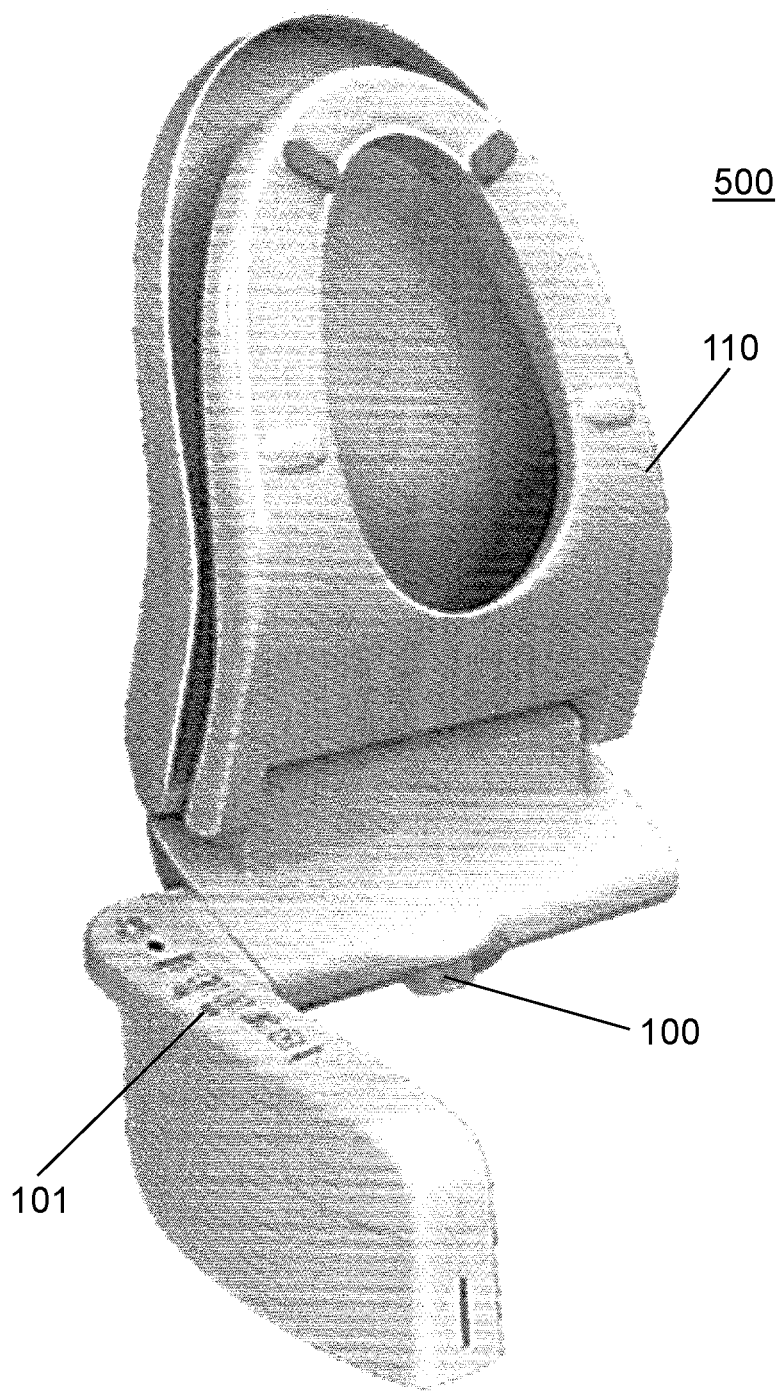
FIG. 12 is a schematic perspective view of a conventional warm-water washing toilet seat.

FIG. 11 is a sectional view of the vicinity of imaging unit 2 on the right side as viewed from the front when toilet seat 10 of excretion detection system 50 according to a third exemplary embodiment of the present disclosure is closed, the sectional view being taken along a vertical direction.

Hereinafter, a configuration of excretion detection system 50 according to the third exemplary embodiment of the present disclosure and toilet seat 10 used therein will be described. Description of a configuration and operation similar to those of the first exemplary embodiment or the second exemplary embodiment will be eliminated.

FIG. 11 illustrates lens cover 7 that is disposed in front of imaging unit 2 in its imaging direction while being inclined with respect to a horizontal plane. When a toilet in which excretion detection system 50 is installed is used and feces 13, urine 14, or private-part washing water 6 falls into toilet bowl 11, water in water reservoir 12 is repelled and adheres to lens cover 7 of imaging unit 2. Lens cover 7 is made of, for example, a transparent material having a low surface frictional resistance.

Such a configuration causes a contamination adhering to lens cover 7 to be likely to move downward by its own weight, so that the contamination adhering thereto deviates from the center of a visual field of imaging unit 2. This reduces decrease in visibility of imaging unit 2, and thus enabling excretion detection performance to be maintained for a long period of time. Lens cover 7 preferably has a surface subjected to water-repellent treatment or antifouling treatment.

In the present exemplary embodiment, excretion detection system 50 includes toilet bowl 11, toilet seat 10 that is openable and provided on toilet bowl 11, imaging unit 2 installed in toilet seat 10, lens cover 7 that protects a lens of imaging unit 2, and information processor 15 that estimates at least one of presence or absence of excrement, and properties of the excrement, using imaging data of imaging unit 2. Toilet seat 10 used in excretion detection system 50 of the present exemplary embodiment is openable and provided on toilet bowl 11. Toilet seat 10 used in excretion detection system 50 of the present exemplary embodiment includes imaging unit 2 provided on its back surface, lens cover 7 that protects the lens of imaging unit 2, and information processor 15 that estimates at least one of presence or absence of excrement, and properties of the excrement using the imaging data of imaging unit 2. Excretion detection system 50 of the present exemplary embodiment and toilet seat 10 used therein include lens cover 7 that is provided while being inclined with respect to the horizontal plane.

Such a configuration enables moving urine, feces, water droplets, or the like attached to the lens of imaging unit 2 from near the center of the visual field of imaging unit 2 by its own weight, so that deterioration in visibility of imaging unit 2 can be reduced, and excretion detection performance can be maintained for a long period of time.

From the above disclosure contents, the present disclosure also includes the following exemplary embodiments and technical ideas.

Toilet seat 10 alone constituting excretion detection system 50 is also an example of the exemplary embodiment of the present disclosure. That is, toilet seat 10 according to the example of the exemplary embodiment of the present disclosure is configured to be attached to toilet bowl 11. Toilet seat 10 is configured such that a holding position can be switched between a state where toilet seat 10 is erected on an upper surface of toilet bowl 11 and a state where toilet seat is substantially horizontal. Toilet seat 10 includes imaging unit 2 provided on its back surface, and information processor 15. Imaging unit 2 may be composed of the configuration exemplified in each of the first to third exemplary embodiments, or an image sensor. Information processor 15 includes one or more processors, and one or more memories. The one or more memories are provided inside with a program instruction executable by the one or more processors. The program instruction includes at least one of the following steps (a) to (d). The program instruction is configured to operate toilet seat 10 by performing at least one of steps (a) to (d) using one or more processors. Step (a) includes a step of acquiring imaging data from imaging unit 2. Step (b) includes a step of determining whether toilet seat 10 is erected or is substantially horizontal. Step (c) includes a step of acquiring imaging data from imaging unit 2 when toilet seat 10 is in the substantially horizontal state. Step (d) includes a step of not acquiring imaging data from imaging unit 2 when toilet seat 10 is in the standing state.

Toilet seat 10 may further include blocking part 21. Blocking part 21 may be composed of the configuration exemplified in each of the first to third exemplary embodiments, or a light shield. Blocking part 21 is configured to block imaging visual field 3 of imaging unit 2 when toilet seat 10 is erected on the upper surface of toilet bowl 11. Blocking part 21 is configured not to block imaging visual field 3 of imaging unit 2 when toilet seat 10 is substantially horizontal to the upper surface of toilet bowl 11.

In the first to third exemplary embodiments, "toilet seat 10 is erected" described above is described as "toilet seat 10 is opened" or "toilet seat 10 opens", and "toilet seat 10 is horizontal" is described as "toilet seat 10 is closed" or "toilet seat 10 closes".

As described above, the present disclosure provides an excretion detection system having an excretion detection function and a health information presentation function, and a toilet seat used therein. Thus, the excretion detection system of the present disclosure and the toilet seat used therein can be widely used for toilets in nursing homes, hospitals, general homes, and the like.

What is claimed is:

1. An excretion detection system comprising:
a toilet bowl;
a toilet seat that is openable and provided on the toilet bowl;
a toilet seat open-close detector configured to detect whether the toilet seat is opened or closed;
a seating detector configured to detect a seated state and a non-seated state of a user, the seating detector being independent of the toilet seat open-close detector;
an imaging unit with which the toilet seat is provided; and
an information processor that estimates at least one selected from the group consisting of (i) presence or absence of excrement and (ii) a property of the excrement, using imaging data of the imaging unit, the imaging unit being configured not to capture an image at least when the toilet seat is opened.

2. The excretion detection system according to claim 1, wherein the imaging unit is configured not to capture an image while the toilet seat is opened based on a detection result of the toilet seat open-close detector.

3. The excretion detection system according to claim 1, wherein the imaging unit is configured not to capture an image when the seating detector detects that the user does not sit on the toilet seat.

4. The excretion detection system according to claim 1, further comprising a blocking part that blocks an imaging visual field of the imaging unit, wherein the blocking part is configured to block the imaging visual field of the imaging unit when the toilet seat is opened.

5. The excretion detection system according to claim 4, wherein the blocking part is provided at a position where the imaging visual field of the imaging unit is blocked when the toilet seat is opened.

6. The excretion detection system according to claim 1, further comprising an imaging notification unit that notifies capturing an image using the imaging unit.

7. An excretion detection system comprising:
a toilet bowl;
a toilet seat that is openable and provided on the toilet bowl;
at least one imaging unit with which the toilet seat is provided; and
an information processor that estimates at least one selected from the group consisting of (i) presence or absence of excrement and (ii) a property of the excrement, using imaging data of the at least one imaging unit, the at least one imaging unit comprising a plurality of imaging units,
wherein the plurality of imaging units include a first imaging unit disposed on a left side with respect to a center line that extends from a front side to a back side of the toilet seat, and a second imaging unit disposed on a right side with respect to the center line.

8. An excretion detection system comprising:
a toilet bowl;
a toilet seat that is openable and provided on the toilet bowl;
an imaging unit with which the toilet seat is provided;
a toilet seat open-close detector configured to detect whether the toilet seat is opened or closed;
a seating detector configured to detect a seated state and a non-seated state of a user, the seating detector being independent of the toilet seat open-close detector;
an information processor that estimates at least one selected from the group consisting of (i) presence or absence of excrement and (ii) a property of the excrement, using imaging data of the imaging unit; and
a toilet seat deformation preventing structure provided around the imaging unit configured to prevent deformation of the toilet seat at the position of the imaging unit.

9. An excretion detection system comprising:
a toilet bowl;
a toilet seat that is openable and provided on the toilet bowl;
an imaging unit with which the toilet seat is provided;
a toilet seat open-close detector configured to detect whether the toilet seat is opened or closed;
a seating detector configured to detect a seated state and a non-seated state of a user, the seating detector being independent of the toilet seat open-close detector;
a lens cover that protects a lens of the imaging unit; and
an information processor that estimates at least one selected from the group consisting of (i) presence or absence of excrement and (ii) a property of the excrement, using imaging data of the imaging unit, the lens cover being provided while being inclined with respect to a horizontal plane.

10. An excretion detection system comprising:
a toilet bowl;
a toilet seat that is openable and provided on the toilet bowl;
an imaging unit with which the toilet seat is provided;
a toilet seat open-close detector configured to detect whether the toilet seat is opened or closed;
a seating detector configured to detect a seated state and a non-seated state of a user, the seating detector being independent of the toilet seat open-close detector;
a lens cover that protects a lens of the imaging unit; and
an information processor that estimates at least one selected from the group consisting of (i) presence or absence of excrement and (ii) a property of the excrement, using imaging data of the imaging unit, the excretion detection system detecting that an imaging visual field of the imaging unit is blocked by a predetermined area or more and notifying a user of the blocked imaging visual field.

11. The excretion detection system according to claim 2, wherein the imaging unit is configured not to capture an image when the seating detector detects that the user does not sit on the toilet seat.

12. The excretion detection system according to claim 2, further comprising a blocking part that blocks an imaging visual field of the imaging unit, wherein the blocking part is configured to block the imaging visual field of the imaging unit when the toilet seat is opened.

13. The excretion detection system according to claim 3, further comprising a blocking part that blocks an imaging visual field of the imaging unit, wherein the blocking part is configured to block the imaging visual field of the imaging unit when the toilet seat is opened.

14. The excretion detection system according to claim 12, wherein the blocking part is located at a position where the imaging visual field of the imaging unit is blocked when the toilet seat is opened.

15. The excretion detection system according to claim 13, wherein the blocking part is provided at a position where the imaging visual field of the imaging unit is blocked when the toilet seat is opened.

16. A toilet seat constituting the excretion detection system according to claim 1.

17. A toilet seat constituting the excretion detection system according to claim 2.

18. A toilet seat constituting the excretion detection system according to claim 5.

19. A toilet seat constituting the excretion detection system according to claim 7.

20. The excretion detection system according to claim 1, wherein the seating detector is configured to be pushed by the toilet bowl when a user sits on the toilet seat and applies weight thereto, and the seating detector protrudes from the toilet seat when the user does not sit.

* * * * *